(12) United States Patent
Geerlings et al.

(10) Patent No.: US 10,828,124 B2
(45) Date of Patent: Nov. 10, 2020

(54) ILLUMINATION SYSTEMS

(71) Applicant: Gentex Corporation, Zeeland, MI (US)

(72) Inventors: Kurtis L. Geerlings, Zeeland, MI (US); Thomas S. Wright, Holland, MI (US); David M. Falb, Grand Rapids, MI (US); Christopher J. Adamski, Holland, MI (US); Jeremy A. Schut, Grand Rapids, MI (US); William L. Tonar, Holland, MI (US); Jason D. Hallack, Allendale, MI (US); Michael J. Metivier, Jenison, MI (US); Brian J. Beardsley, Holland, MI (US)

(73) Assignee: GENTEX CORPORATION, Zeeland, MI (US)

( * ) Notice: Subject to any disclaimer, the term of this patent is extended or adjusted under 35 U.S.C. 154(b) by 70 days.

(21) Appl. No.: 16/116,973

(22) Filed: Aug. 30, 2018

(65) Prior Publication Data
US 2019/0060026 A1 Feb. 28, 2019

Related U.S. Application Data

(60) Provisional application No. 62/552,778, filed on Aug. 31, 2017.

(51) Int. Cl.
*A61B 90/30* (2016.01)
*A61B 90/00* (2016.01)
*F21V 33/00* (2006.01)
*F21W 131/205* (2006.01)
(Continued)

(52) U.S. Cl.
CPC ............ *A61B 90/30* (2016.02); *A61B 90/361* (2016.02); *A61B 90/39* (2016.02); *F21V 33/0068* (2013.01); *A61B 2034/2048* (2016.02); *A61B 2034/2065* (2016.02); *A61B 2090/309* (2016.02); *A61B 2090/363* (2016.02); *A61B 2090/3612* (2016.02); *A61B 2090/3614* (2016.02); *A61B 2090/3983* (2016.02); *A61B 2090/502* (2016.02); *F21W 2131/205* (2013.01)

(58) Field of Classification Search
None
See application file for complete search history.

(56) References Cited

U.S. PATENT DOCUMENTS 8,905,585 B2    12/2014    Dallam et al.
9,222,257 B2    12/2015    Dallam et al.
(Continued)

FOREIGN PATENT DOCUMENTS

WO          0035402       6/2000
WO    2013111134 A1   8/2013

*Primary Examiner* — Elmito Breval
(74) *Attorney, Agent, or Firm* — Price Heneveld LLP; Bradley D. Johnson (57) ABSTRACT

An illumination system for a medical suite comprises a light assembly comprising at least one illumination source configured to selectively direct a light emission in a region of the surgical suite. The system further comprises an imager configured to capture image data in a field of view in the medical suite. A controller is in communication with the light assembly and the imager. The controller is configured to detect a location of the marker in the image data and control the light assembly to direct the light emission within the region based on the location of the marker.

19 Claims, 4 Drawing Sheets

(51) Int. Cl.
*A61B 90/50* (2016.01)
*A61B 34/20* (2016.01)

(56) References Cited

U.S. PATENT DOCUMENTS

| | | | |
|---|---|---|---|
| 2009/0040366 A1* | 2/2009 | Voelker | A61B 90/35 |
| | | | 348/370 |
| 2012/0206050 A1 | 8/2012 | Spero | |
| 2012/0259178 A1 | 10/2012 | Kim et al. | |
| 2015/0198797 A1* | 7/2015 | Andre | A61B 5/7425 |
| | | | 348/80 |
| 2018/0111265 A1* | 4/2018 | DelSpina | A61B 90/50 |
| 2018/0150960 A1* | 5/2018 | Derda | G06T 7/73 |
| 2018/0231227 A1* | 8/2018 | Strolin | F21V 23/0457 |
| 2019/0021797 A1* | 1/2019 | Dyer | A61B 34/20 |

* cited by examiner

ILLUMINATION SYSTEMS

CROSS-REFERENCE TO RELATED APPLICATION

This application claims the benefit of and priority to U.S. Provisional Patent Application No. 62/552,778, filed on Aug. 31, 2017, entitled ILLUMINATION SYSTEMS, the entire disclosure of which is hereby incorporated herein by reference.

FIELD OF THE DISCLOSURE

The present disclosure generally relates to illumination systems, and more particularly, to surgical theater and surgical suite illumination systems.

BACKGROUND OF THE DISCLOSURE

Artificial lighting provided in surgical theaters and surgical suites may present a number of issues with regard to positioning, shadows, luminosity and glare. Often, medical professionals are not stationary and the lighting needs to be dynamic due to the shifting of personnel and instruments throughout the surgical procedure. Further, differences in the physical dimensions of personnel may make positioning light sources challenging. Accordingly, new illumination systems for surgical suites may be advantageous.

SUMMARY OF THE PRESENT DISCLOSURE

According to one aspect of this disclosure, an illumination system for a medical suite is disclosed. The system comprises a light assembly comprising at least one illumination source configured to selectively direct a light emission in a region of the surgical suite. The system further comprises an imager configured to capture image data in a field of view in the medical suite. A controller is in communication with the light assembly and the imager. The controller is configured to detect a location of the marker in the image data and control the light assembly to direct the light emission within the region based on the location of the marker.

According to another aspect of this disclosure, a method for controlling a lighting system in a medical suite is disclosed. The method comprises identifying a location for a light emission by positioning a marker in an operating region of the medical suite. The method further comprises directing the light emission to the location and tracking the location of a marker in response to a movement of the marker. The method further comprises directing the light emission to follow the movement of the marker maintaining an illumination of the location.

According to yet another aspect of this disclosure, an illumination system for a medical suite is disclosed. The system comprises a light assembly comprising at least one illumination source configured to selectively direct a light emission in a region of the surgical suite. The system further comprises an imager configured to capture image data in a field of view in the medical suite and an emitter configured to emit a detection emission in the field of view. A controller is in communication with the light assembly and the imager. The controller is configured to activate the detection emission to radiate the field of view and identify a reflection of the detection emission in the image data. The controller is further configured to determine a location of the marker in the image data based on the reflection and control the light assembly to direct the light emission within the region based on the location of the marker.

These and other aspects, objects, and features of the present disclosure will be understood and appreciated by those skilled in the art upon studying the following specification, claims, and appended drawings. It will also be understood that features of each example disclosed herein may be used in conjunction with, or as a replacement for, features of the other examples.

BRIEF DESCRIPTION OF THE DRAWINGS

The following is a description of the figures in the accompanying drawings. The figures are not necessarily to scale, and certain features and certain views of the figures may be shown exaggerated in scale or in schematic in the interest of clarity and conciseness.

In the drawings.

DETAILED DESCRIPTION

Additional features and advantages of the invention will be set forth in the detailed description which follows and will be apparent to those skilled in the art from the description or recognized by practicing the invention as described in the following description together with the claims and appended drawings.

As used herein, the term "and/or," when used in a list of two or more items, means that any one of the listed items can be employed by itself, or any combination of two or more of the listed items, can be employed. For example, if a composition is described as containing components A, B, and/or C, the composition can contain A alone; B alone; C alone; A and B in combination; A and C in combination; B and C in combination; or A, B, and C in combination.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Referring generally to FIGS. 1-4, the disclosure provides for an illumination system 10. The illumination system 10 may comprise a controller 12 and various accessories that may be utilized in a medical suite 14 to selectively illuminate a location or operating region 16. The illumination system 10 may comprise one or more light assemblies 18, which may include one or more light sources 20. Additionally, the system 10 may comprise at least one imager 22 operable to capture image data in a field of view comprising the operating region 16. In an exemplary embodiment, the controller 12 of the system 10 may be configured to scan the operating region 16 to identify a location of a marker 24. Based on the location of the marker 24, the controller 12 may control a lighting emission from the one or more light sources 20 to illuminate the location corresponding to the position of the marker 24 identified in the image data. In this way, the system 10 may provide for a computer assisted control of a direction of lighting emissions directed from the one or more light sources to conveniently illuminate various locations within the operating region 16.

Figure 1:
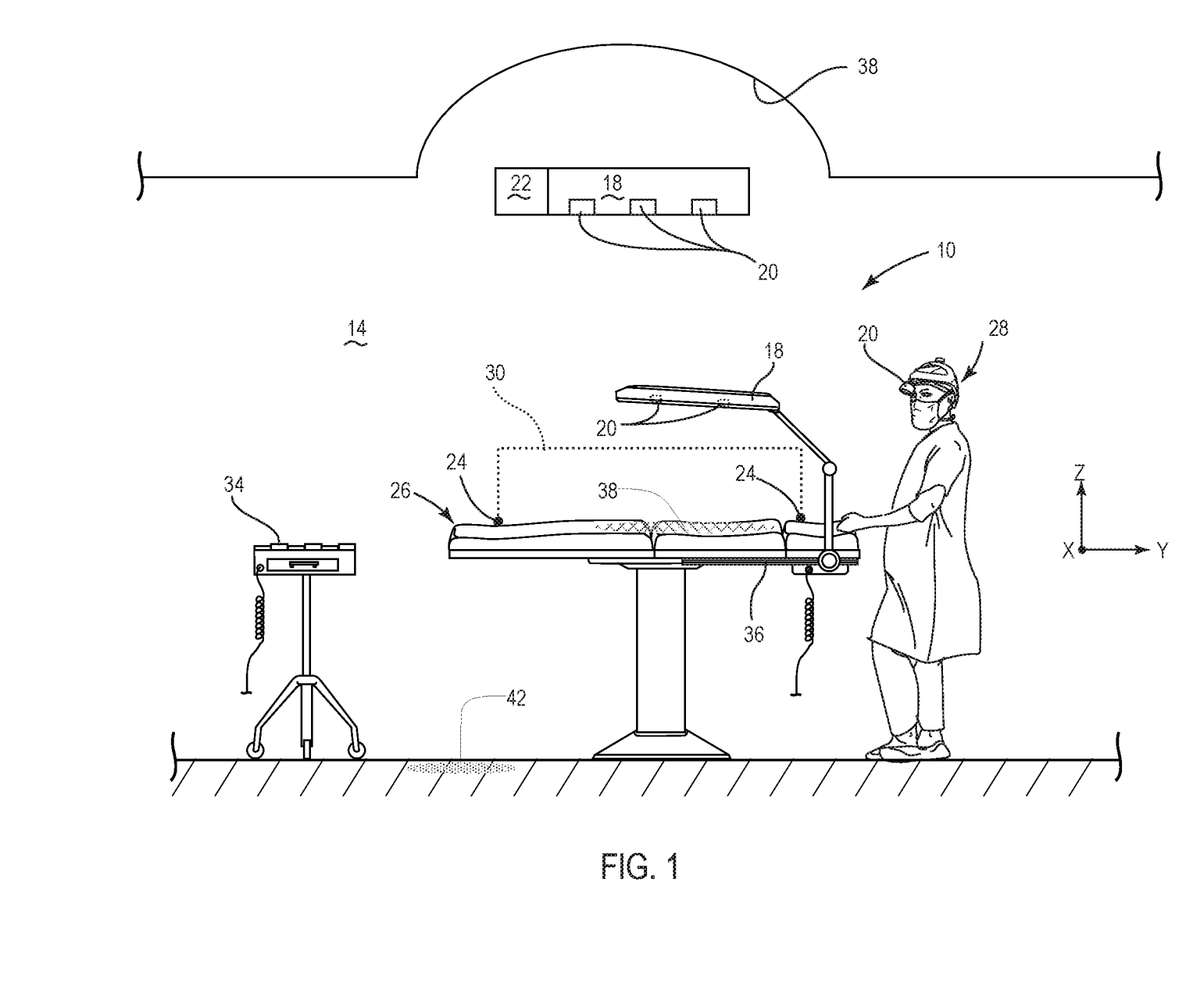
FIG. 1 is a schematic view of a surgical suite utilizing an illumination system.

Referring now to FIG. 1, reference numeral 10 generally designates an illumination system 10. The illumination system 10 is depicted in a medical suite 14 and includes one or more light assemblies 18. The light assemblies 18 may include one or more light sources 20. The illumination system 10 may include one or more imagers 22 depicted to aid in the use of the illumination system 10. The imagers 22 may be positioned within or coupled to the light assemblies 18 (e.g., in handles or bodies), a table 26, a wearable device 28 and/or around the medical suite 14. The imager 22 may be a charge-coupled device (CCD) imager, a complementary metal-oxide semiconductor (CMOS) imager, other types of imagers and/or combinations thereof. According to various examples, the imager 22 may include one or more lenses to collimate and/or focus the light reflected by the patient, the table 26 or other features of the medical suite 14. The table 26 may at least partially define the operating region 16 or a surgical field 30. For purposes of this disclosure, the operating region 16 may be an operating field which is an isolated area where surgery is performed and may include all furniture and equipment covered with sterile drapes and all personnel being properly attired. Positioned within the medical suite 14 may be one or more instruments 34 or tools as explained in greater detail below. Although described in connection with the medical suite 14, it will be understood that the illumination system 10 of the present disclosure may be utilized in a variety of environments. For example, the illumination system 10 may be utilized in automobile repair areas, doctor's offices, dentistry, photography studios, manufacturing settings, as well as other areas where dynamic lighting solutions may be advantageous.

The table 26 is configured to support a patient during a surgical procedure. According to various examples, the table 26 may have a square, rectangular and/or oval configuration. The table 26 may be composed of a metal (e.g., stainless steel), a polymer and/or combinations thereof. According to various examples, a sterile covering (e.g., a cloth or paper) may be positioned across a surface of the table 26. The table 26 may be configured to tilt, rotate and/or be raised or lowered. In examples where the table 26 is configured tilt, the table 26 may tilt an angle from about 1° to about 10° about a long or a short axis of the table 26. The tilting of the table 26 may be performed in conjunction with illumination provided from the illumination system 10 and/or the light assemblies 18. For example, the table 26 may be configured to tilt toward and/or away from the light assemblies 18 to increase illumination, decrease illumination and/or to eliminate glare reflecting off of the patient and/or table 26. Further, tilting of the table 26 may be advantageous in allowing users (e.g., medical personnel) positioned around the table 26 to more easily access the patient and/or surgical field. In addition to tilting, it will be understood that the table 26 may be configured to raise or lower, rotate and/or slide about an X-Y plane.

The light assemblies 18 may take a variety of configurations. The light assemblies may include one or more light sources 20. In a first example, the light assemblies 18 may be modular and interconnected and supported on a track system. For example, the light assemblies 18 may have a circular, oval, oblong, triangular, square, rectangular, pentagonal or higher order polygon shape. It will be understood that different light assemblies 18 may take different shapes and that the illumination system 10 may include a variety of light assemblies 18. The track system of the light assemblies 18 may allow for one or more light assemblies 18 to be moved relative to other light assemblies 18. The shape of the light assemblies 18 may be configured to allow the light assemblies 18 to "fit" or mate together along edges of the light assemblies 18. For example, square or triangular light assemblies 18 may be grouped in contact with one another or separated to form a larger shape (e.g., a cross, pentagon, freeform, etc.).

According to various examples, the light assemblies 18 may be configured to snap together, or otherwise electrically and/or mechanically connect to one another. For example, the light assemblies 18 may share electrical power with one another once connected. The light assemblies 18 may be lighter than conventional lighting solutions. Several advantages may be derived from the use of the modular example of the light assemblies 18. First, use of modular light assemblies 18 may allow for dynamic and large scale lighting arrangements to be formed from the smaller modular light assemblies 18. Second, as the light assemblies 18 are positioned on the track assembly, the light assemblies 18 may have a greater range of movement and/or positionability as compared to conventional lighting systems. For example, while traditional lighting solutions may be attached to an extension which limits how far it may be moved, the track system allows a lighting assembly 18 to be moved from one end of the table 26 to another. Third, as some of the light assemblies 18 may mate together along long edges, gaps (e.g., dead space) between light assemblies 18 may be minimized and/or eliminated. Fourth, in examples where the light assemblies 18 are connected to share power, cords or other cumbersome power transfer devices may be eliminated.

In yet another example, the light assemblies 18 may be positioned on, or include, gimbaled arms which can be adjusted and extended outward. It will be understood that additionally or alternatively, one or more gimbals may connect the light assembly 18 to the arm. For example, one or more light assemblies 18 may be gimbaled on an arm and independently movable from the arm. The arm of the light assemblies 18 may be connected to a ceiling, a wall and/or a floor of the medical suite 14 or connected to the table 26. The gimbal(s) of the light assemblies 18 may allow X-, Y- and/or Z-direction movement of the light assembly 18 with respect to the arm. As will be explained in greater detail below, the light assemblies 18 may be automatically, or electronically, manipulated with respect to the arm and/or may be manually manipulated by hand relative to the arm. Examples which utilize multiple light assemblies 18 may be advantageous in reducing shadowing which is produced by one or more of the light assemblies 18. Further, use of the gimbal to connect the light assembly 18 with the arm may be advantageous in allowing a greater range of motion of the light assembly 18 compared to conventional lighting systems.

In yet another example, the light assemblies 18 may be connected to one or more movable assemblies. For example, the movable assemblies may be tethered or untethered to walls and/or a ceiling of the medical suite 14. It will be understood that one or more of the movable assembly examples of the light assembly 18 may be utilized within the medical suite 14 without departing from the teachings provided herein. In untethered examples, the movable assembly may be a drone or other unmanned aerial vehicle configured to be moved about the medical suite 14. For example, the drone may include fans, blades and/or other propulsion systems which are configured to move the drone within the open space of the medical suite 14. Such an untethered example of the movable assembly may be advantageous in allowing a constantly shifting and dynamically positionable light assembly 18 which is free to move about the medical suite 14. In tethered examples of the movable assembly, the movable assembly may be coupled to one or more cables. The cables may be retracted, extended, or ridden along by the movable assembly to allow the shifting of position of the light assembly 18 in the movable assembly. The cables may extend from the ceiling and/or walls of the medical suite 14. The movable assembly examples of the light assemblies 18 may be controlled remotely (e.g., from a person) or may be controlled automatically by a computer or other controller. Once the movable assembly examples of the light assembly 18 are no longer needed, the movable assembly may be stored within the ceiling, walls and/or storage cabinets of the medical suite 14.

Figure 2:
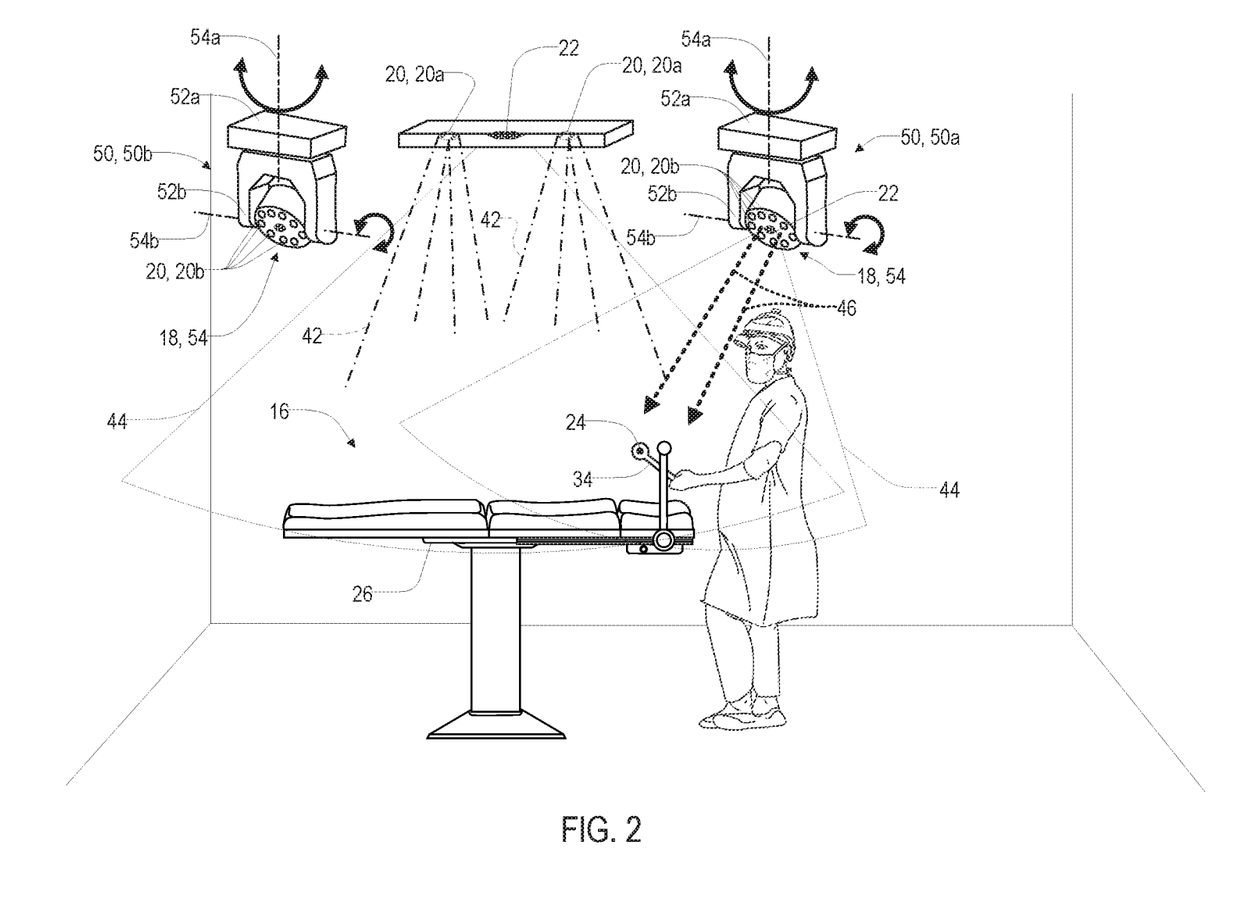
FIG. 2 is a schematic view of an illumination system for a surgical suite demonstrating a marker configured to identify at least one illumination region.

Referring now to FIG. 2, an additional embodiment of the illumination system 10 is shown demonstrating an example of a tracking routine. As previously discussed, the tracking routine may comprise identifying the marker 24 in the operating region 16. In operation, the working region may be illuminated by a detection emission 42, which is projected in a field of view 44 of the imager 22. The detection emission 42 may be emitted from one or more of the light sources 20 in a substantially non-visible wavelength of light. In an exemplary embodiment, the detection emission 42 may be emitted from a detection emitter 20a as infrared light (e.g., near-infrared, infrared, and/or far-infrared). In this configuration, the operating region 16 may be illuminated by the detection emission 42 illuminating various objects that enter the field of view 44 of the imager 22. Accordingly, the marker 24 may be illuminated by the detection emission 42 from the emitter 20a such that the reflected light from the detection emission 42 is captured in the image data of the imager 22. To improve an intensity of the detection emission 42 reflected back to the imager 22, in some embodiments, the marker 24 may comprise a reflective surface finish configured to reflect the detection emission 42.

With the marker 24 illuminated by the detection emission 42 in field of view 44, the imager 22 may capture the reflection of the marker 24 in image data. In some embodiments, the imager 22 may comprise one or more filters that may limit the transmission of wavelengths of light that are not included in the detection emission 42 such that the reflection of the detection emission 42 may be readily identifiable. Once the image data comprising the reflection of the marker 24 is captured, the image data may be communicated to the controller 12 such that the location of the marker 24 may be identified in the field of view 44. Based on the location of the marker 24, the controller 12 may control a lighting emission 46 from the one or more light sources 20 to illuminate the location corresponding to the position of the marker 24. The light sources 20 configured to emit the lighting emission 46 may be referred to as visible light sources 20b. In this way, the system 10 may provide for a computer assisted control of a direction of lighting emissions directed from the one or more light sources to conveniently illuminate various locations within the operating region 16.

In various embodiments, the illumination system 10 may include one or more imagers 22 which capture image data from the medical suite 14 and/or from the operating region 16. The imagers 22 may be configured to relay image data to the controller 12 of the illumination system 10. The controller 12 may include a memory and a processor. The memory may store computer executable commands (e.g., routines) which are controlled by the processor. According to various examples, the memory may include a light control routine and/or an image analyzing routine. The image analyzing routine is configured to process data from the imager 22. For example, the image analyzing routine may be configured to identify shadows and luminosity of the operating region 16, the light from the guidance system, location of points of interest (e.g., users around the table 26, the wearable device 28) and/or gestures from the users.

According to various examples, the image analyzing routine may also be configured to identify the location of the marker 24 in the image data. The marker 24 may include one or more symbols, computer readable codes and/or patterns which designate a point of interest in the image data. For example, the marker 24 can be positioned around the operating region 16 or the surgical field 30 such that the image analyzing routine may identify the location of the marker 24 in the operating region 16. The marker 24 may be disposed on one or more of the instruments 34, the users, points of interest in the medical suite 14 and/or the patient. The image analyzing software may or may not track light from the guidance system outside of the perimeter indicated by the markers 24 and/or the operating region 16.

Once the image analyzing routine has processed the data from the imager 22, the light control routine may control how the light assemblies 18 are operated. For example, the light control routine may be configured to move, steer, activate or otherwise influence the light assemblies 18 to emit light at the location of the marker 24. Such a location may correspond to an area of interest where the user is looking or working (e.g., as measured from the guidance system). In this way, the light control routine may steer or otherwise move the one or more visible light sources 20b to emit the lighting emission 46 to illuminate various areas where the user is looking and/or where hands and instruments 34 are positioned.

In some embodiments, the controller 12 of the system 10 may be configured to track the position of the marker 24 and/or various instruments 34 in the operating region 16 and the medical suite 14. For example, the instruments 34 and the marker 24 may comprise a radio frequency identification and tracking device configured to communicate a radio signal, which may be located by one or more communication circuits in communication with the controller 12. In various embodiments, a location of the instruments 34 and/or markers 24 may be tracked in the operating region 16 by tracking (e.g. triangulating) a position of each of the instruments 34 or markers 24 in the suite 14. Once the location of the marker 24 or instrument 34 is identified in the medical suite 14, the controller 12 may control the light assemblies 18 to emit light at the location of the marker 24 and/or instruments 34.

Still referring to FIG. 2, in some embodiments, the system 10 may comprise one or more positioning assemblies 50, which may be positioned in connection with a ceiling of the medical suite 14 above the operating region 16. As shown, the system 10 comprises a first positioning mechanism 50a and a second positioning mechanism 50b. In general, the positioning assemblies 50 as discussed herein may be configured to control a direction of one or more lighting emissions 46 emitted from the one or more visible light sources 20b. As demonstrated and further discussed in reference to FIG. 4, each of the light sources 20 as well as the positioning assemblies 50 may be in communication with the controller 12, which may be configured to control a direction of the one or more lighting emissions 46 to illuminate the location of the marker 24 with visible light. In this way, the system 10 may be operable to control one or more of the visible light sources 20b to illuminate the marker 24 or various portions of the operating region 16.

In various embodiments, the one or more positioning assemblies 50 may comprise one or more gimbaled arms, which may be maneuvered or adjusted in response to a movement (e.g., rotational actuation) of one or more actuators 52a and 52b. In this configuration, the controller 12 may be configured to control each of the actuators 52a and 52b to manipulate the orientation of a lighting module 54 comprising one or more of the visible light sources 20b. In this way, the positioning assembly 50 may control the rotation of the lighting module 54 about a first axis 54a and a second axis 54b. Such manipulation of the lighting module 54 may enable the controller 12 to direct the light sources 20b to selectively illuminate the operating region 16 or various portions of the medical suite 14 in response to the detected location of the marker 24.

The positioning assemblies 50 and actuators 52a and 52b, as discussed herein, may correspond to one or more electrical motors (e.g., servo motors, stepper motors, etc.). Accordingly, each of the positioning assemblies 50 (e.g., the actuators 52) may be configured to rotate the lighting module 360 degrees or within the boundary constraints of lighting modules 54 or other support structures that may support the lighting modules 54. The controller 12 may control the motors or actuators 52 of the lighting modules 54 to direct the lighting emissions 46 of the visible light sources 20b to target a desired location in the medical suite 14. In order to accurately direct the lighting module 54 to target the desired location, the controller 12 may be calibrated to control the position of the lighting module 54 to target locations in a grid or work envelope of the medical suite 14. The calibration of such a system may require maintenance in the form of calibration updates or compensation due to variations in operation of the positioning assemblies 50 and actuators 52 that may occur over time.

Figure 3:
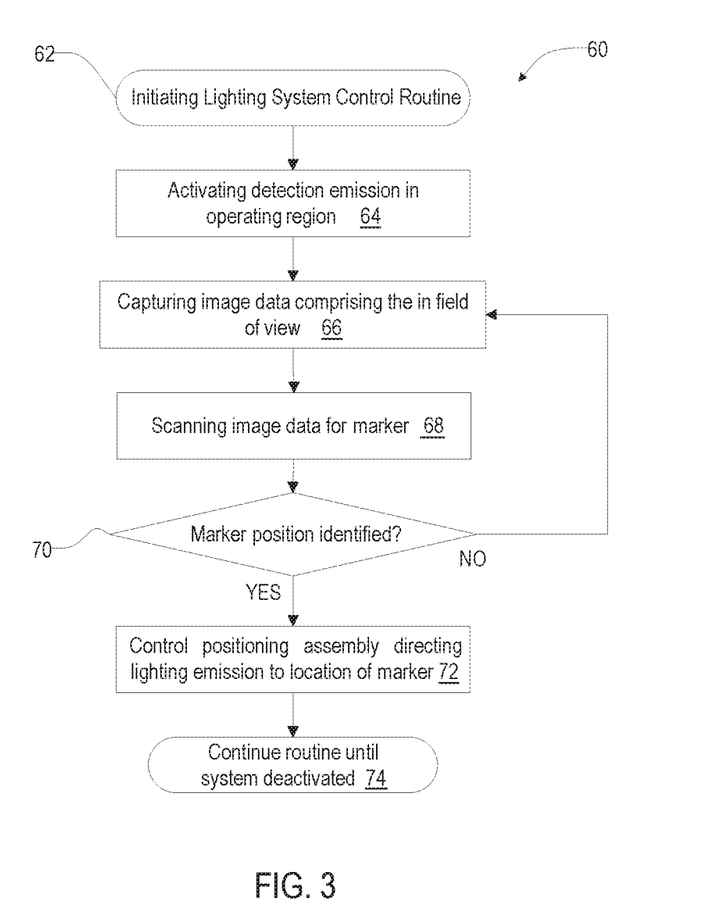
FIG. 3 is a flow chart demonstrating a method for controlling an illumination system.

Referring to FIG. 3, a flow chart for a method 60 for controlling the system 10 is demonstrated. In operation, the method 60 may begin by initializing a control routine of the illumination system 10 (62). Once initiated, the controller 12 may activate the emitter 20a to illuminate the operating region 16 in the detection emission 42 (64). In this way, the operating region 16 may be illuminated by the detection emission 42 illuminating various objects that enter the field of view 44 of the imager 22. The controller 12 may then control the imager 22 to capture image data in the field of view 44 (66). Once the image data is captured, the controller 12 may process or scan the image data for various objects including the marker 24.

In step 70, the controller 12 may determine if the position of the marker 24 is identified in the image data. If the position of the marker is not identified, the method 60 may return to steps 66 and 68 to capture and scan the image data in the field of view 44. If the position of the marker 24 is identified in step 70, the controller 12 may control one of more of the positioning assemblies 50 to activate the lighting emission(s) 46 directed at the marker 24 (72). Once the position of the marker 24 is identified and illuminated by the lighting emission(s) 46, the controller 12 may continue to track the location of the marker 24 and reposition the positioning assemblies 50 to maintain a consistent illumination of the marker 24 and the corresponding location (74).

Figure 4:
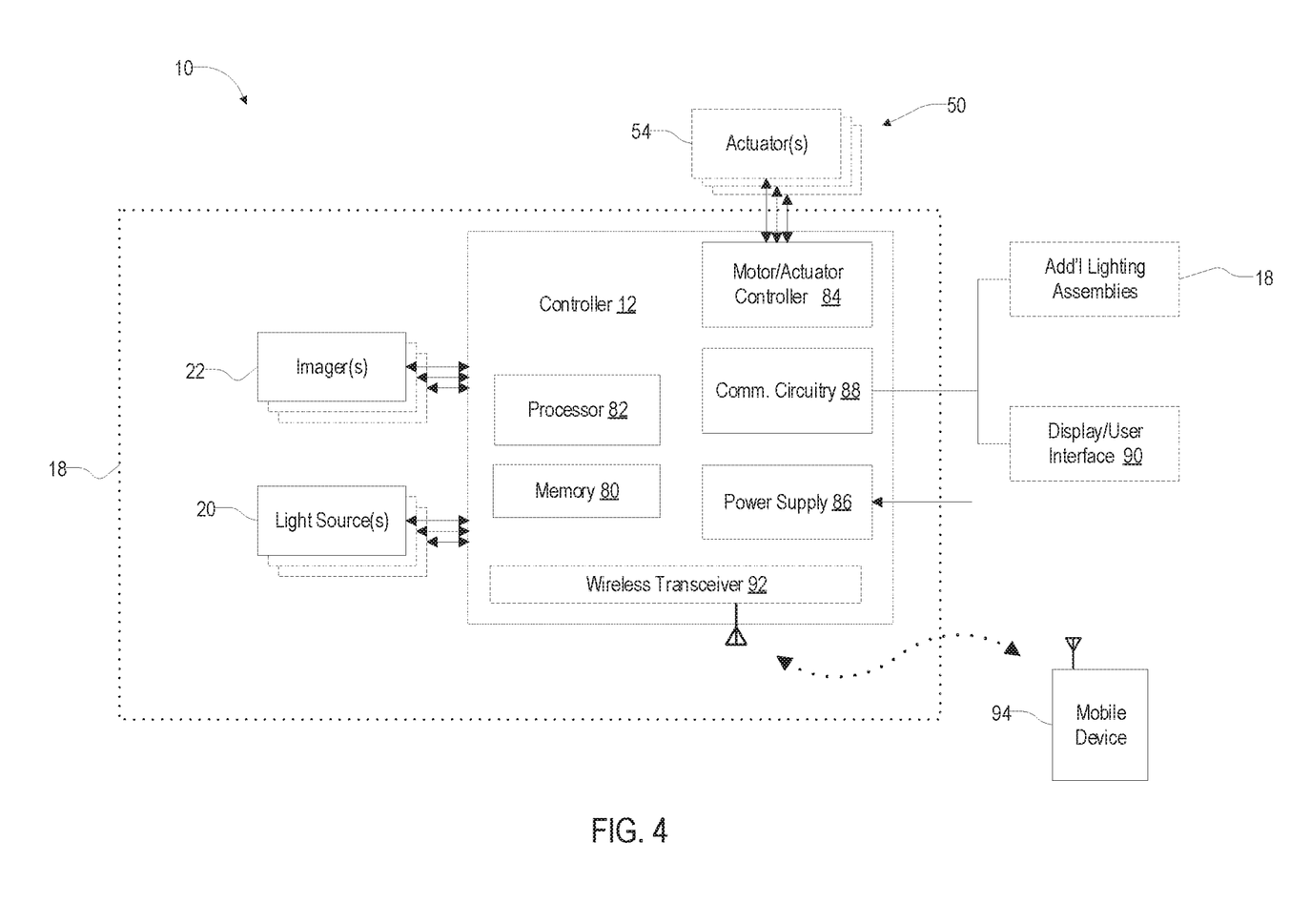
FIG. 4 is a block diagram demonstrating the illumination system in accordance with the disclosure.

Referring to FIG. 4, a block diagram of an illumination system 10 is shown. As discussed herein, the illumination system 10 may include one or more imagers 22 configured to capture image data from the medical suite 14 and/or from the operating region 16. The imagers 22 may be configured to relay visual information to the controller 12 of the illumination system 10. The controller 12 may include a memory 80 and a processor 82. The memory 80 may store computer executable commands (e.g., routines) which are controlled by the processor 82. According to various examples, the memory 80 may include a light control routine and/or an image analyzing routine. In exemplary embodiments, the memory 80 may include the lighting control routine 62.

Once the image analyzing routine has processed the image data from the imager 22, the controller 12 may communicate one or more control instructions to a motor or actuator controller 84. In response to the control signals, the motor controller 84 may control the actuators 52a, 52b or the positioning assemblies 50 to move, steer, or otherwise adjust an orientation of the light assemblies 18. In this way, the controller 12 may direct the lighting assemblies 18 to emit the lighting emission 46 and/or direct the field of view 44 to a desired location, which may correspond to the location of the marker 24. The system 10 may additionally comprise one or more power supplies 86. The power supplies 86 may provide for one or more power supplies or ballasts for various components of the lighting assembly 18 as well as the actuators 52a, 52b or positioning assemblies 50.

In some embodiments, the system 10 may further comprise one or more communication circuits 88, which may be in communication with the processor 82. The communication circuit 88 may be configured to communicate data and control information to a display or user interface 90 for operating the system 10. The interface 90 may comprise one or more input or operational elements configured to control the system 10 and communicate data. The communication circuit 88 may further be in communication with additional lighting assemblies 18, which may operate in combination as an array of lighting assemblies. The communication circuit 88 may be configured to communicate via various communication protocols. For example, communication protocols may correspond to process automation protocols, industrial system protocols, vehicle protocol busses, consumer communication protocols, etc. Additional protocols may include, MODBUS, PROFIBUS, CAN bus, DATA HIGHWAY, DeviceNet, Digital multiplexing (DMX512), or various forms of communication standards.

In various embodiments, the system 10 may comprise a variety of additional circuits, peripheral devices, and/or accessories, which may be incorporated into the system 10 to provide various functions. For example, in some embodiments, the system 10 may comprise a wireless transceiver 92 configured to communicate with a mobile device 94. In such embodiments, the wireless transceiver 92 may operate similar to the communication circuit 88 and communicate data and control information for operating the system 10 to a display or user interface of the mobile device 94. The wireless transceiver 92 may communicate with the mobile device 94 via one or more wireless protocols (e.g. Bluetooth®; Wi-Fi (802.11a, b, g, n, etc.); ZigBee®; and Z-Wave®; etc.). In such embodiments, the mobile device 94 may correspond to a smartphone, tablet, personal data assistant (PDA), laptop, etc.

In various embodiments, the light sources 20 may be configured to produce unpolarized and/or polarized light of one handedness including, but not limited to, certain liquid crystal displays (LCDs), laser diodes, light-emitting diodes (LEDs), incandescent light sources, gas discharge lamps (e.g., xenon, neon, mercury), halogen light sources, and/or organic light-emitting diodes (OLEDs). In polarized light examples of the light sources 20, the light sources 20 are configured to emit a first handedness polarization of light. According to various examples, the first handedness polarization of light may have a circular polarization and/or an elliptical polarization. In electrodynamics, circular polarization of light is a polarization state in which, at each point, the electric field of the light wave has a constant magnitude, but its direction rotates with time at a steady rate in a plane perpendicular to the direction of the wave.

As discussed, the light assemblies 18 may include one or more of the light sources 20. In examples including a plurality of light sources 20, the light sources 20 may be arranged in an array. For example, an array of the light sources 20 may include an array of from about 1×2 to about 100×100 and all variations therebetween. As such, the light assemblies 18 including an array of the light sources 20 may be known as pixelated light assemblies 18. The light sources 20 of any of the light assemblies 18 may be fixed or individually articulated. The light sources 20 may all be articulated, a portion may be articulated, or none may be articulated. The light sources 20 may be articulated electro-mechanically (e.g., a motor) and/or manually (e.g., by a user). In static, or fixed, examples of the light sources 20, the light sources 20 may be assigned to focus on various predefined points (e.g., on a patient and/or on the table 26).

Referring back again to FIG. 1, various exemplary embodiments of the system 10 are discussed to demonstrate the versatility of the lighting system 10. For example, the medical suite 14 may include one or more light assemblies 18 configured as table lights. In such an example, the light assemblies 18 may be configured as a table-mounted light which flip-up into the surgical field. The light assemblies 18 may be coupled directly to the table 26 and/or be positioned on a track 36 coupled with the table 26. Track examples of the light assemblies 18 may be advantageous in allowing the light assemblies 18 to be slid and/or translated along the table 26 without need to disconnect the light assemblies 18. The light assemblies 18 may be operable between an undeployed (e.g., under the table 26) position and a deployed (e.g., over the table 26 and/or in the operating region 16) position. According to various examples, the light assembly 18 may be positioned on an arm which is configured to be bent, rotated and/or is flexible. Further, the arm of the flip-up light assembly 18 may be automated to move (e.g., autonomously and/or by the control of an operator). For example, the light assembly 18 may be configured to move to follow a surgeon positioned proximate the table 26.

According to yet another example, the light assembly 18 may be configured as a movable screen. In such an example, the light assembly 18 may include a central viewing port through with to see and one or more light sources 20 extending around a portion, a majority or fully around a perimeter of the viewing portion. In such an example, the light sources 20 may be positioned on a patient side of the light assembly 18. The light sources 20 may form a light ring that can illuminate an area of interest from various angles. The angles may also be controllable by a user, allowing light from all angles or just a portion. This will help prevent unnecessary illumination, can help avoid glare and/or may help visual contrast of certain activities. The light assembly 18 may be positioned on a movable arm or extension such that the light assembly 18 may be positioned in various locations around the patient. The viewing portion may include a transparency which is configured to block and/or enhance one or more wavelengths or wavelength bands of visible and/or non-visible light. Further, the transparency may be configured to magnify light passing through the transparency. Magnification may be advantageous in providing a user of the light assembly 18 a better view of a small incision or other surgical procedure. Such a movable screen example of the light assembly 18 may be advantageous in decreasing shadowing (e.g., due to the use of multiple light sources 20 positioned away from each other) on a designated area.

In yet another example, the light assembly 18 may be configured to operate in conjunction with a mirror 38. The mirror 38 may be positioned above the table 26. In the depicted example the mirror 38 is positioned with the ceiling of the medical suite 14, but it will be understood that the mirror 38 may additionally or alternatively be suspended above the table 26. According to various examples, the mirror 38 may be concave such that light emitted by the light assembly 18 may be collimated and reflected toward the table 26 and/or the patient. In such an example, the light assembly 18 may include one or a plurality of light sources 20 positioned in a ring and configured to emit light toward the mirror 38. The light sources 20 may be positioned proximate a perimeter of the mirror 38 and/or proximate the table 26. Such an example of the light assembly 18 may be advantageous in allowing the light sources 20 and/or light assembly 18 to be positioned in unconventional locations away from a ceiling of the medical suite 14.

In yet another example, the light assembly 18 has a semi-circular configuration. The semi-circular configuration may be advantageous in allowing the light assembly 18 to be rotated such that the light sources 20 may be positioned to reduce shadowing.

In yet another example, the light assembly 18 may be configured to be positioned within an opening (e.g., an incision and/or cavity) of the patient. Such an example may be referred to as an in situ light assembly 18. In such an example, the light assembly 18 may be spherical, columnar, cuboid and/or other shapes. The light assembly 18 may be clear, transparent, transmissive and/or opaque. For example, a majority of the light assembly 18 may be clear or transmissive to emit light, while a portion may be opaque (e.g., to prevent light from shining in a surgeon's eyes). The light assembly 18 may generate light via chemical or electrical forces. Further, it will be understood that the light assembly 18 may include one or more of the light sources 20. In some examples, the light assembly 18 may include a magnetic recovery option (e.g., to ease in removal from the patient) and/or a radio-frequency identification tag to aid in location of the light assembly 18. Such an example of the light assembly 18 may be advantageous in providing light directly where it is needed (e.g., inside of the patient).

It will be understood that any and/or all of the light assemblies 18 described above may be used in connection with another. For example, the medical suite 14 may include the movable assembly examples, the flip-up examples and/or the movable screen examples without departing from the teachings provided herein. In another example, the light assemblies 18 can be positioned within the patient and separate light assemblies 18 may be configured to emit light toward the mirror 38. Further, the various features of the examples of the light assemblies 18 may be combined without departing from the teachings provided herein. For example, one or more of the flip-up light examples may include the transparency of the movable screen through which to look. In another example, the movable assembly light assemblies 18 may initially be coupled to a gimbaled arm until instructed to begin hovering over the patient.

As explained above, the light assemblies 18 may include one or more light sources 20 configured to emit visible and/or non-visible light. For example, the light sources 20 may be configured to emit visible light, infrared light (e.g., near-infrared and/or far-infrared) and/or ultraviolet light. In some examples, the light sources 20 may be strobed at a controlled frequency. Visible light examples of light from the light sources 20 may have a color temperature of from about 1,700 K to about 27,000 K. The color temperature of one or more of the light sources 20 may be variable across the color temperature range. In examples of the light sources 20 configured to emit infrared light, the infrared light may be used with one or more guidance systems (e.g., scanning and control systems) as described in greater detail below. In examples of the light sources 20 which emit ultraviolet light, the ultraviolet light alone, or in combination with other features (e.g., $TiO_2$ coatings, films and/or paints), may be configured to provide cleaning, sanitation and/or sterilization of surfaces (e.g., the table 26, instruments 34, the light assembly 18 and/or other portions of the medical suite 14). For example the ultraviolet light may be used in a photocatalytic process to kill bacteria, viruses and/or to eliminate dirt and grime. The light sources 20 may be light-emitting diodes, incandescent bulbs, and or other light emitting sources. The light sources 20 may also be configured to emit light which excites a fluorescent dye. In such examples, the light may be referred to as an excitation emission. The excitation emission may be infrared, visible and/or ultraviolet light. In such examples, a fluorescent dye may be applied within the surgical site (e.g., incision or open cavity) of the patient such that application of the excitation emission to the patient causes the surgical site to fluoresce in visible light. Further, a biodegradable powder may be applied to the surgical site in the patient which may carry the fluorescent dye and/or be configured to reduce glare by scattering light off wet surfaces. In such an example, the biodegradable powder may be clear such that the underlying tissues are still visible, but alters the reflection of light such that the light is not specularly reflected and perceived as glare.

According to various examples, one or more of the light sources 20 is a light engine capable of producing unpolarized and/or polarized light of one handedness including, but not limited to, certain liquid crystal displays (LCDs), laser diodes, light-emitting diodes (LEDs), incandescent light sources, halogen light sources and/or organic light emitting diodes (OLEDs). In polarized light examples of the light sources 20, the light sources 20 are configured to emit a first handedness polarization of light. According to various examples, the first handedness polarization of light may have a circular polarization and/or an elliptical polarization. In electrodynamics, circular polarization of light is a polarization state in which, at each point, the electric field of the light wave has a constant magnitude, but its direction rotates with time at a steady rate in a plane perpendicular to the direction of the wave. A circularly polarized wave can be in one of two possible states, right handedness circular polarization in which the electric field vector rotates in a right-hand sense with respect to the direction of propagation, and left handedness circular polarization in which the vector rotates in a left-hand sense. Using the handedness convention, left or right handedness is determined by pointing one's left or right thumb toward the source, against the direction of propagation, and then matching the curling of one's fingers to the temporal rotation of the field. Elliptically polarized light may also be described as having a handedness in a substantially similar manner to that of the circularly polarized examples, but the electric vector varies in magnitude during rotation. Circular polarization of the light may be achieved when linearly polarized light from the light sources 20 passes through an integral or separate quarter-wave plate. Additionally or alternatively, a reflective polarizer may be utilized. If a reflective polarizer is used on the light sources 20, as opposed to an absorbing polarizer, the light emitted by the light sources 20 that is the "wrong" polarization (e.g., the second handedness polarization of light) is reflected back into the light source 20 where it can be "depolarized" and reflected back toward the polarizer.

In polarized examples of the light sources 20, as the surgical site of the patient is illuminated by the first handedness polarization of light from the light sources 20, the moisture or water present within the patient may tend to specularly reflect the first handedness polarization of light as the second handedness polarization of light. As explained above, the first handedness of polarization, once specularly reflected off of the patient may reverse in handedness to form the second handedness polarization of light and be perceived by a human and/or machine (e.g., the imager 22) observer as glare. Generally glare is the effect caused by the specular reflection of illumination light off of a smooth surface such as a surface film of water. This glare can visually mask the details of the object below the reflecting surface and can obscure surrounding objects because the "glare" image appears brighter than surrounding objects. The reflected second handedness polarization of light may be opposite from the first handedness polarization of light. In examples where the first handedness polarization of light is circularly polarized, the first and second polarizations of light are circularly polarized opposite from one another. In other words, the first and second polarizations of light may have an opposite handedness (e.g., left handedness and right handedness). As will be explained in greater detail below, an optical filter may be incorporated into the wearable device 28, into a filter positioned between the user and the patient, the imager 22 and/or into the movable screen example of the light assembly 18.

As explained above, the light assemblies 18 may include one or more of the light sources 20. In examples including a plurality of light sources 20, the light sources 20 may be arranged in an array. For example, an array of the light sources 20 may include an array of from about 1×2 to about 100×100 and all variations therebetween. As such, the light assemblies 18 including an array of the light sources 20 may be known as pixelated light assemblies 18.

The light sources 20 of any of the light assemblies 18 may be fixed or individually articulated. The light sources 20 may all be articulated, a portion may be articulated, or none may be articulated. The light sources 20 may be articulated electromechanically (e.g., a motor) and/or manually (e.g., by a user). In static, or fixed, examples of the light sources 20, the light sources 20 may be assigned to focus on various predefined points (e.g., on a patient and/or on the table 26).

According to various examples, the light sources 20 may be rastered over the patient to provide illumination where desired. In other words, the light emitted from the light sources 20 may be steered. The light sources 20 may be rastered by mechanical, optical and/or electro-optical methods. In a first example, the light sources 20 may be mechanically moved via one or more motors. In a second example, one or more mirrors may be optically coupled to one or more light sources 20 and configured to raster the emitted light into a steerable beam. The beam is then rastered across the patient. In a third example, the emitted light may be steered using a liquid crystal element. In such an example, the liquid crystal element may essentially collimate or spreads out the emitted light, or steer the light in a particular direction. Further, the liquid crystal element may function as a variable lens. Such a liquid crystal element may be advantageous in that the light sources 20 may not need to mechanically be moved and may eliminate mechanical connections. Further, such a liquid crystal element could be utilized to retro-fit existing light sources 20 and light assemblies 18. Rastering the light from the light sources 20 may be advantageous in providing control of light intensity in various locations (e.g., points of interest on the patient). For example, the light may be rastered slower in areas to provide a higher perceived intensity and faster in areas to create a lower perceived intensity. Such a feature may be advantageous in giving the perceived appearance of variable light intensity using a single light source 20. Further, as the light may be steered, a single light source may offer a high level of adjustability for different kinds of surgeries as it can be steered and adjusted as demanded.

In yet another example, the light assembly 18 and/or light sources 20 may be coupled with an array of reflective elements similar to a digital light projection system. The reflective elements may be mirrors which are transitioned between on and off states to reflect the emitted light from the light sources 20. By switching the mirrors between on and off (e.g., reflective and non-reflective) states, light can be reflected to various areas to change intensity and/or lighting patterns. It will be understood that the reflected light may also form an image on the patient which may be utilized in augmented reality. It will also be understood that galvanometers may be used in conjunction with the reflective elements.

It will be understood that any and all features described in connection with the light sources 20 may be applied to any and all of the examples of the light assemblies 18. For example, the in situ light assembly 18 may include pixelated and/or independently movable light sources 20 while the movable assembly light assembly 18 may emit polarized light. Further, the steerable examples of the light sources 20 may be applied to any of the light assembly 18 examples.

According to various examples, one or more users positioned within the medical suite 14 may include the wearable device 28. The wearable device 28 may be eyewear (e.g., goggles, eye glasses), headwear (e.g., a face shield, helmet, visor, etc.), a garment and/or combinations thereof. In eyewear examples, the wearable device 28 may be configured to enhance (e.g., by increased transmission) or eliminate one or more wavelengths or wavelength bands of light. For example, when using the fluorescent dye explained above, the wearable device 28 may allow all light of the wavelength emitted from the fluorescent dye to pass through the wearable device 28. Such a feature may be advantageous in allowing a greater visibility of the fluorescent dye which may result in a higher perceived luminance of the surgical site.

In another example, the wearable device 28 may be configured to eliminate one or more polarizations of light. As explained above, specularly reflected circularly polarized light which flip handedness. The wearable device 28 may be configured to allow the first handed polarization of light to pass, while eliminating the second handedness polarization of light to minimize glare. According to various examples, polarization filtering may be accomplished by an optical filter within the wearable device 28. The optical filter is configured to reflect and/or absorb the second handedness polarization of light. The optical filter may include one or more reflective polarizers and/or absorptive polarizers. In such examples, the optical filter may be referred to as a polarizer. Reflective polarizer examples may include a wire grid polarizer plus a quarter wave plate or optical retarder, a multilayer plastic film such as a dual brightness enhancement film (DBEF) polarizer with a quarter wave plate, an optical retarder and/or a liquid crystal material. DBEF film or absorbing polarizer examples of the optical film may have a transmittance of ambient light and/or the first handedness polarization of light incident on the optical filter of about 5%, 10%, 20%, 30%, 40%, 45%, 49%, 50%, 60%, 70%, 80%, 90% or greater than about 99%. Further, the optical filter may have a reflectance and/or absorbance of about 5%, 10%, 20%, 30%, 40%, 45%, 49%, 50%, 60%, 70%, 80%, 99% or greater of the second handedness polarization of light. Removal of the second handedness polarization of light may reduce and/or eliminate a perceived glare off of the surgical site. The color of the first handedness polarization of light which passed through the optical filter may be fairly neutral gray to avoid influencing the natural visible colors.

According to various examples, the wearable device 28 may be shuttered and linked to one or more of the light assemblies 18 and the illumination system 10 to provide different lighting for different users. For example, in strobed examples of the light sources 20, different wearable devices 28 may provide different shutter speeds and delays such that a perceived intensity of the light is different for different users. Such a feature may be programmed into the wearable device 28 or may be adjusted dynamically during surgery.

According to various examples, the wearable device 28 may be configured to reflect and/or to emit light. In reflective examples, the wearable device 28 may include a mirror or other reflective surface configured to collect, reflect, redirect and/or collimate light from one or more of the light assemblies 18. For example, the reflective element of the wearable device 28 may include one or more galvanometers and/or gyroscopes which change the reflection axis of the reflective element to redirect the light from the light assembly 18 to where the wearer is looking. Additionally or alternatively, the wearable device 28 may include one or more light sources 20. Efficiency of the light sources 20 may be increased by turning the light sources 20 on and off based on whether the wearer is looking at the operating region 16, only turning on light sources 20 that are pointed at the region 16 or field 30 (e.g., while shutting off light sources 20 that are pointing away) and/or by adjusting the intensity of light based on measured lighting and/or shadowing of the area the user is looking at. According to various examples, the wearable device 28 may be lighter and/or have an increased battery time compared to conventional lighting systems. Further, the wearable device 28 may be cordless. Further, the wearable device 28, in eyewear examples, may provide magnification of light.

According to various examples, the wearable device 28 may include one or more guidance systems. The guidance systems may include a feature to indicate where the wearer is looking and/or working. For example, the guidance system may include a laser emitting visible and/or nonvisible (e.g., infrared) light. The light emitted from the guidance system may be tracked by the imager 22 and relayed to the illumination system 10. Such tracking of the light emitted from the guidance system may allow the illumination system 10 to emit light from the light assemblies 18 where the user is looking.

As explained above, the illumination system 10 may include one or more imagers 22 which capture image data from the medical suite 14 and/or from the operating region 16. The imagers 22 may be configured to relay visual information to a controller of the illumination system 10. The controller may include a memory and a processor. The memory may store computer executable commands (e.g., routines) which are controlled by the processor. According to various examples, the memory may include a light control routine and/or an image analyzing routine. The image analyzing routine is configured to process data from the imager 22. For example, the image analyzing routine may be configured to identify shadows and luminosity of the operating region 16, the light from the guidance system, location of points of interest (e.g., users around the table 26, the wearable device 28) and/or gestures from the users.

According to various examples, the image analyzing routine may also be configured to identify the location of a plurality of markers 24 within the image. The markers 24 may be symbols, computer readable codes and/or patterns which designate a point of interest in the image. For example, a plurality of markers 24 can be positioned around the operating region 16 or the surgical field 30 such that the image analyzing routine may determine the perimeter of the operating region 16. Further, one or more markers 24 may be positioned on the instruments 34, the users, points of interest in the medical suite 14 and/or the patient. The image analyzing software may or may not track light from the guidance system outside of the perimeter indicated by the markers 24 and/or the operating region 16.

Once the image analyzing routine has processed the data from the imager 22, the light control routine may control how the light assemblies 18 are operated. For example, the light control routine may be configured to move, steer, activate or otherwise influence the light assemblies 18 to emit light where the user is looking or working (e.g., as measured from the guidance system). In a first example, the light control routine may steer or otherwise move the emitted light from the light sources 20 to track where the user is looking and/or where hands and instruments 34 are positioned. The light control routine may slow the speed of movement of the light relative to the movement of the user's gaze to minimize uncomfortable fast switching of illumination. In a second example, when the user's gaze is detected outside of the operating region 16, the light assemblies 18 may be configured to emit light toward a last known gaze position. Further, the light control routine may be configured to switch off one or more light sources 20 positioned on the wearable device 28 to conserve its power. Third, the light control routine may control one or more of the lighting assemblies 18 based on gesture control. For example, where the light from different lighting assemblies 18 is directed may be indicated by gestures (e.g., displaying a single finger at a point where a first light source 20 should shine and displaying two fingers at a location where a second light source 20 should shine). Other exemplary gestures which the light control routine may respond to may include pinching to enlarge or contract the light beam. Steering of the light from the light sources 20 may be accomplished by any of the methods outlined above. In another example, the light control routine may respond to the location and orientation of markers 24 positioned on the user (e.g., on a head or hands/gloves). For example, illumination from the light assemblies 18 may be moved or altered based on the head and/or hand orientation of the user. Further, the light control routine may be configured to direct or steer light from one or more of the light sources 20 to the reflector of the wearable device 28. For example by monitoring the user and movement of the marker 24, the image analyzing routine may determine where the reflector is and emit light at the appropriate angle towards it to illuminate the surgical site. In a fourth example, one or more of the imagers 22 may be a visible light camera which can detect shadowing and the light control routine may alter the illumination accordingly. For example, the light control routine may auto adjust the intensity of one or more of the light sources 20 if another light source 20 gets blocked or begins producing shadows. It will be understood that the light control routine may also be controlled via voice or mechanical input (e.g., foot) without departing from the teachings provided herein. In a fifth example, the light control routine may be configured to turn off one or more lights automatically. For example, if the light control routine detects that a light source 20 will shine in a user's eyes or produce glare due to the angle of the light and positioning of a user, the light control routine will automatically turn off the offending light source and compensate by activating other light sources 20 and/or increasing the luminance of the other light sources.

In yet other examples, the imager 22 may be used in conjunction with one or more infrared emitters. An infrared emitter may project a field of infrared dots into the medical suite 14 which may be read by the imager 22. By knowing the location of the emitter and by reading the positioning of the dots, the light control and/or image analyzing routines may create a three-dimensional map of the surgical suite. With the three-dimensional map, any of the above noted light control routine operations may be performed.

The illumination system 10 and/or the disclosure provided above are configured to operate in conjunction with a number of other features present in the medical suite 14. For example, the illumination system 10 may be configured to track the location and use of the instruments 34. For example, the instruments 34 may include a paint, marker and/or indicator which can be seen (e.g., infrared reflective and/or fluorescent) by the imager 22. The instruments 34 may be coded based on type (e.g., consumable tool vs. non-consumable) and/or by the operator using or placing them. The instruments 34 may be tracked as they enter and exit the surgical field 30 by showing them to imager 22. In yet other examples, one or more of the instruments 34 may include a radio frequency identification tracking device.

Modifications of the disclosure will occur to those skilled in the art and to those who make or use the disclosure. Therefore, it is understood that the embodiments shown in the drawings and described above are merely for illustrative purposes and not intended to limit the scope of the disclosure, which is defined by the following claims as interpreted according to the principles of patent law, including the doctrine of equivalents.

It will be understood by one having ordinary skill in the art that construction of the described disclosure, and other components, is not limited to any specific material. Other exemplary embodiments of the disclosure disclosed herein may be formed from a wide variety of materials, unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature, or may be removable or releasable in nature, unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system 10 may be varied, and the nature or numeral of adjustment positions provided between the elements may be varied. It should be noted that the elements and/or assemblies of the system 10 may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes, or steps within described processes, may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further, it is to be understood that such concepts are intended to be covered by the following claims, unless these claims, by their language, expressly state otherwise. Further, the claims, as set forth below, are incorporated into and constitute part of this Detailed Description.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the end-points of each of the ranges are significant both in relation to the other end-point, and independently of the other end-point.

The terms "substantial," "substantially," and variations thereof as used herein are intended to note that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other, such as within about 5% of each other, or within about 2% of each other.

What is claimed is:

1. An illumination system for a medical suite, comprising:
   a light assembly comprising at least one illumination source configured to selectively direct a light emission in a region of the surgical suite;
   an emitter configured to emit a detection emission in a non-visible wavelength of light;
   an imager configured to capture image data in a field of view in the medical suite, wherein the imager is configured to capture the non-visible wavelength of the detection emission reflected from the marker to identify the marker in the image data, wherein the imager comprises a filter configured to inhibit a plurality of wavelengths of light emphasizing the detection emission reflected from the marker in the image data;
   a controller in communication with the light assembly and the imager, wherein the controller is configured to:
      detect a location of a marker in the image data based on the detection emission reflected from the marker; and
      control the light assembly to direct the light emission within the region based on the location of the marker.

2. The illumination system according to claim 1, further comprising a positioning mechanism, wherein the positioning mechanism is configured to control a direction of the light emission.

3. The illumination system according to claim 2, wherein the controller is in communication with the positioning mechanism and configured to control a direction of the light emission to the location of the marker.

4. The illumination system according to claim 2, wherein the positioning mechanism comprises a multi-axis actuator configured to direct the light emission in the region.

5. The illumination system according to claim 1, wherein the field of view is directed in the surgical suite such that the location of the marker identifies the portion of the region of the surgical suite illuminated by the light emission.

6. The illumination system according to claim 1, wherein the light assembly is configured to mount to a ceiling of the medical suite above the field.

7. The illumination system according to claim 1, wherein the light assembly is configured to direct the light emission to a portion of an operating table located in the region of the medical suite.

8. The illumination system according to claim 1, wherein the detection emission comprises light in the infrared or near-infrared range.

9. The illumination system according to claim 1, wherein the marker comprises a reflective surface configured to reflect the detection emission.

10. The illumination system according to claim 1, wherein the marker is disposed on a hand-held instrument.

11. The illumination system according to claim 1, wherein the controller is further configured to:
    detect a location of the marker in response to a signal communicated from the marker, wherein the location of the marker is identified in response to a radio frequency communication from the marker.

12. The illumination system according to claim 11, wherein the controller is further configured to:

identify an object or shadow in the field of view based on the image data proximate to the location in the region.

13. A method for controlling a lighting system in a medical suite comprising:
   emitting a detection emission in a non-visible wavelength of light into an operating region;
   capturing image data in a field of view in the operating region, wherein the image data comprises the non-visible wavelength of the detection emission reflected from the filtering a plurality of wavelengths of light in the image data generating filtered image data limiting the wavelengths of light that are not included in the detection emission;
   identifying a location of a marker in the operating region of the medical suite in the filtered image data;
   directing the light emission to the location;
   tracking the location based on a position of a marker in response to a movement of the marker, wherein the location is identified based on a radio frequency based position identification of the marker; and
   directing the light emission to follow the movement of the marker maintaining an illumination of the location.

14. The method according to claim 13, further comprising:
   capturing image data in a field of view directed in the operating region.

15. The method according to claim 14, further comprising:
   identifying a shadow location of a shadow in the operating region proximate to the location based on the image data.

16. The method according to claim 14, further comprising:
   emitting a detection emission into the field of view, wherein the detection emission comprises non-visible wavelength of light.

17. The method according to claim 16, wherein the detection emission comprises light in the infrared or near-infrared range.

18. The illumination system according to claim 14, further comprising:
   reflecting the detection emission from the marker;
   identifying the reflection of the detection emission in the image data; and
   determining a location of the marker based on the reflection.

19. An illumination system for a medical suite, comprising: a light assembly comprising at least one illumination source configured to selectively direct a light emission in a region of the surgical suite; an emitter configured to emit a detection emission in a non-visible wavelength of the detection emission reflected from a marker; wherein the imager comprises a filter configured to inhibit a plurality of wavelengths of light emphasizing the detection emission reflected from the marker in the image data; a controller in communication with the light assembly and the imager, wherein the controller is configured to: activate the detection emission to radiate the field of view, wherein the detection emission comprises non-visible wavelength of light; identify a marker based on a reflection of the detection emission in the image data; determine a location of the marker in the image data based on the reflection; and control the light assembly to direct the light emission within the region based on the location of the marker.

* * * * *